United States Patent
Kato

(10) Patent No.: US 8,443,645 B2
(45) Date of Patent: May 21, 2013

(54) BENDING METHOD AND BENDING APPARATUS FOR MEDICAL SUTURING NEEDLE

(75) Inventor: Kazuaki Kato, Utsunomiya (JP)

(73) Assignee: MANI, Inc., Utsunomiya-shi, Tochigi (JP)

(*) Notice: Subject to any disclaimer, the term of this patent is extended or adjusted under 35 U.S.C. 154(b) by 447 days.

(21) Appl. No.: 12/672,722

(22) PCT Filed: Aug. 29, 2008

(86) PCT No.: PCT/JP2008/065502
§ 371 (c)(1),
(2), (4) Date: Feb. 9, 2010

(87) PCT Pub. No.: WO2009/028651
PCT Pub. Date: Mar. 5, 2009

(65) Prior Publication Data
US 2011/0030435 A1     Feb. 10, 2011

(30) Foreign Application Priority Data

Aug. 29, 2007   (JP) ................. 2007-222856

(51) Int. Cl.
*B21B 15/00* (2006.01)
*B21G 3/30* (2006.01)
(52) U.S. Cl.
USPC ............................................. 72/168; 72/169
(58) Field of Classification Search ............ 72/127, 72/133, 135, 137, 166, 168, 169, 189, 389.2, 72/306
See application file for complete search history.

(56) References Cited

U.S. PATENT DOCUMENTS 5,626,043 A * 5/1997 Bogart et al. .............. 72/133

FOREIGN PATENT DOCUMENTS

| JP | 57-175026 A | | 10/1982 |
|---|---|---|---|
| JP | 63-73989 A | | 4/1988 |
| JP | 63076719 A | * | 4/1988 |
| JP | 4-270021 A | | 9/1992 |
| JP | 9-61322 A | | 3/1997 |
| JP | 3078339 B2 | | 8/2000 |
| JP | 2-42286 B2 | | 9/2009 |
| JP | 2001-314933 A | | 11/2009 |

OTHER PUBLICATIONS

International Search Report in the corresponding International Appl. No. PCT/JP2008/065502.

* cited by examiner

*Primary Examiner* — Debra Sullivan
(74) *Attorney, Agent, or Firm* — Smith Patent Office

(57) ABSTRACT

A bending method and a bending apparatus are provided for bending a medical suturing needle into different curved shapes by using one bending roller. The bending apparatus comprises a reciprocally rotatable bending roller, and a belt having such a flexibility as can be wound on the outer circumference of the bending roller. The bending method curves a medical suturing needle by sandwiching and constricting a material for the medical suturing needle between the bending roller and the belt and by rotating the bending roller reciprocally in the winding direction and in the rewinding direction. In the bending method, the curved shape of the material is changed by changing the winding angle of the belt to be wound on the outer circumference of the bending top thereby to change the area for constricting the material.

4 Claims, 5 Drawing Sheets

BENDING METHOD AND BENDING APPARATUS FOR MEDICAL SUTURING NEEDLE

TECHNICAL FIELD

The present invention relates to methods and apparatuses for bending medical suturing needles, and in particular, to a bending method and a bending apparatus capable of manufacturing a medical suturing needle, which is curved by performing a bending work on a linear needle-shaped raw material at different curvature radii, by changing the winding angle of a belt with respect to the outer peripheral surface of a bending roller.

BACKGROUND ART

The medical suturing needle used to suture living tissues is generally curved from the needle tip to the proximal end through the trunk portion. The curved shape has substantially the same curvature radius over the entire length, and is formed to a shape (an angle) such as ½ circle (180 degrees), ⅜ circle (135 degrees), or ¼ circle (90 degrees). Plural types of medical suturing needles having different thickness and different length have been proposed, which have a curved shape with different curvature radius for every type.

When manufacturing the medical suturing needle curved in the above manner, an art described in Patent Document 1 is known for the bending method of curving the raw material of a shaft rod-shape. In this art, the shaft rod-shaped raw material is curved by inserting the raw material between a circular column shaped bending roll and a belt having flexibility as can be pressure contacted and wound to the outer circumference of the bending roll, bending the raw material along the outer circumferential surface of the bending roller by winding the raw material with the bending roll and the belt, and thereafter, discharging the bent raw material by rewinding.

As described in Patent Document 2, a bending apparatus including a cylindrical winding roll that defines the curved shape of the medical suturing needle, an auxiliary roll that pressure contacts such winding roll, and a metal belt arranged between the winding roll and the auxiliary roll is used, so that the inserted linear needle-shaped raw material can be bent by inserting the linear needle-shaped raw material between the winding roll and the metal belt and rotating the winding roll by a predetermined angle in a clockwise direction. The winding roll is then rotated in the counterclockwise direction so that the curved medical suturing needle can be taken out.

A bi-curve needle or a medical suturing needle mainly used in the opthalmologic surgery is curved with different curvature radii for the needle tip portion and for the trunk portion. The art described in Patent Document 3 is proposed as one method of bending such medical suturing needle.

In the art described in Patent Document 3, the bending work is performed on the linear needle-shaped raw material, which is formed to a predetermined cross-sectional shape in advance, over a predetermined range from one end side at the largest curvature radius forming the curved shape, the bending work is then performed on the raw material subjected to the bending work over a predetermined range from the end of the raw material at a curvature radius smaller than the above curvature radius, and the bending work is subsequently performed over a predetermined range from the end of the raw material so that the curvature radius sequentially becomes smaller. In this art, a plurality of bending rolls having different curvature radii correspond to the curved shape of the medical suturing needle is prepared, and the bending work is sequentially performed by such bending rolls to rationally perform the bending work.

Patent Document 1: Japanese Patent Publication No. 1295902
Patent Document 2: Japanese Patent Publication No. 2002859
Patent Document 3: Japanese Patent Publication No. 3078339

DISCLOSURE OF THE INVENTION

The medical suturing needle is formed with a needle tip having a sharp distal end or a blunt distal end, and is formed such that the thickness gradually becomes greater from the needle tip to the trunk portion. Thus, in the art described in Patent Documents 1 and 2, the bending work in which the inner diameter side of the curve corresponds to the curvature radius of the outer circumferential surface of the bending roll or the winding roll can be performed by inserting the needle tip between the bending roll or the winding roll and the belt, turning the rolls for a predetermined angle to wind the same, and then rewinding. However, when bending the medical suturing needle having different curved shapes, the bending roll or the winding roll having a curvature radius corresponding to the target curved shape needs to be used. In other words, a medical suturing needle of different curved shapes cannot be bent by the bending roll or the winding roll having a specific curvature radius.

In the bending method described in Patent Document 3, the bi-curve suturing needle curved at different curvature radii in the length direction can be bending worked. In other words, the bending work can be rationally performed regardless to what curve the target medical suturing needle is set. However, the bending work of plural times is required with respect to one raw material, and hence the task is troublesome and cumbersome.

In the bending methods of Patent Documents 1 to 3, the center shaft of the raw material is not curved at the same curvature radius if the raw material is formed to a tapered shape since the outer circumferential surface of the raw material contacts the outer circumferential surface of the bending roll and then curves. In such case as well, however, it is assumed as curved at the same curvature radius in practical use, which is the same in the case of the present invention to be described below.

It is an object of the present invention to provide a bending method and a bending apparatus for bending a medical suturing needle into different curved shapes by using one bending roller.

To solve the above problems, a bending method for a medical suturing needle according to the present invention is a bending method for a medical suturing needle including a reciprocally rotatable bending roller and a belt having such a flexibility as can be wound on an outer circumferential surface of the bending roller, a raw material being curved by sandwiching and constricting the raw material of the medical suturing needle between the bending roller and the belt, and reciprocally rotating the bending roller in a winding direction and a re-winding direction to curve the raw material; wherein a curved shape of the raw material is changed by changing a winding angle, at which the belt is wound to the outer circumferential surface of the bending roller, and changing a constricting region with respect to the raw material.

A bending apparatus for a medical suturing needle according to the present invention includes a reciprocally rotatable bending roller and a belt having such a flexibility as can be pressure contacted and wound on an outer circumferential surface of the bending roller, a winding angle, at which the belt is wound to the outer circumferential surface of the bending roller, being changed.

In the bending apparatus for the medical suturing needle, preferably, the belt having the flexibility is formed long and at least one side of a wound site wound on the bending roller is wound across a roller, and the position of the roller is changed along the outer circumferential surface of the bending roller to change the winding angle at which the belt is wound on the outer circumferential surface of the bending roller.

In the bending apparatus for the medical suturing needle, preferably, the belt having the flexibility is formed long; a pair of constricting members for suspending the belt is arranged; the bending roller is arranged between the pair of constricting members and is position movable in a direction transversing a line connecting the pair of constricting members; and the belt is suspended between the pair of constricting members and the position of the bending roller is changed in the direction transversing the line connecting the pair of constricting members to change the winding angle at which the belt is wound on the outer circumferential surface of the bending roller.

In the bending method for the medical suturing needle (hereinafter referred to as "suturing needle") according to the present invention, the flexible belt is wound on the outer circumferential surface of the reciprocally rotating bending roller, and the bending roller and the belt are rotated in the direction of taking in the raw material with the raw material of the suturing needle sandwiched and constricted between the bending roller and the belt to perform the bending work, where the raw material performed with the bending work can be taken out by rotating in the re-winding direction. The constricting region by the belt can be changed by changing the winding angle of the belt with respect to the outer circumferential surface of the bending roller, thereby changing the degree of the bending work on the raw material and changing the curved shape of the raw material.

In other words, if the winding angle of the belt with respect to the bending roller is large, the raw material is constricted from the sandwiched distal end portion to the tapered portion and the trunk portion, up to the proximal end, where the bending force acts on the constricted portion with the rotation of the bending roller to be subjected to the bending work. The raw material is thus bent to a curved shape corresponding to the curvature radius of the bending roller.

If the winding angle of the belt with respect to the bending roller is small, the raw material sandwiched between the bending roller and the belt is subjected to the bending work with the rotation in the winding direction, but the portion constricted by the bending roller and the belt is local, and thus the bending force acts only at the constricted local area and the bending work is performed only thereto. For instance, if the distal end side of the raw material separates from the wounded portion of the belt and is released from the constriction, the separated portion becomes free and cannot receive the bending force. Thus, the distal end side of the raw material is bent to a curved shape having a curvature radius greater than the curvature radius of the bending roller.

The bending work from a curved shape substantially equal to the curvature radius of the bending roller to a curved shape having a curvature radius greater than the curvature radius of the bending roller can be performed by changing the winding angle of the belt with respect to the bending roller. In particular, the curved shape from the distal end portion of the raw material to the trunk portion through the tapered portion can be changed by changing the winding angle of the belt with respect to the bending roller while performing the bending work on one raw material.

In the bending apparatus for the suturing needle according to the present invention, the bending work of the suturing needle having different curved shapes can be performed as the winding angle at which to wind the belt on the outer circumferential surface of the bending roller can be changed.

In particular, if the belt having the flexibility is formed long and at least one side of a wound site wound on the bending roller of the belt is wound across a roller, and the position of the belt is changed along the outer circumferential surface of the bending roller to change the winding angle at which the belt is wound on the bending roller, the winding angle of the belt with respect to the bending roller can be set by arranging the position of the roller wound with the belt at a desired position with respect to the bending roller. Thus, the suturing needle having different curved shapes can be easily bent.

If the belt having the flexibility is formed long; a pair of constricting members for suspending the belt is arranged; the bending roller is arranged between the pair of constricting members and is position movable in a direction transversing a line connecting the pair of constricting members; and the belt is suspended between the pair of constricting members and the position of the bending roller is changed in the direction transversing the line connecting the pair of constricting members to change the winding angle at which the belt is wound on the outer circumferential surface of the bending roller, the winding angle of the belt with respect to the bending roller can be changed by moving the bending roller in the direction substantially orthogonal to the direction of suspending the belt. Thus, the suturing needle having different curved shapes can be easily bent.

DESCRIPTION OF REFERENCE NUMERALS

Figure 1:
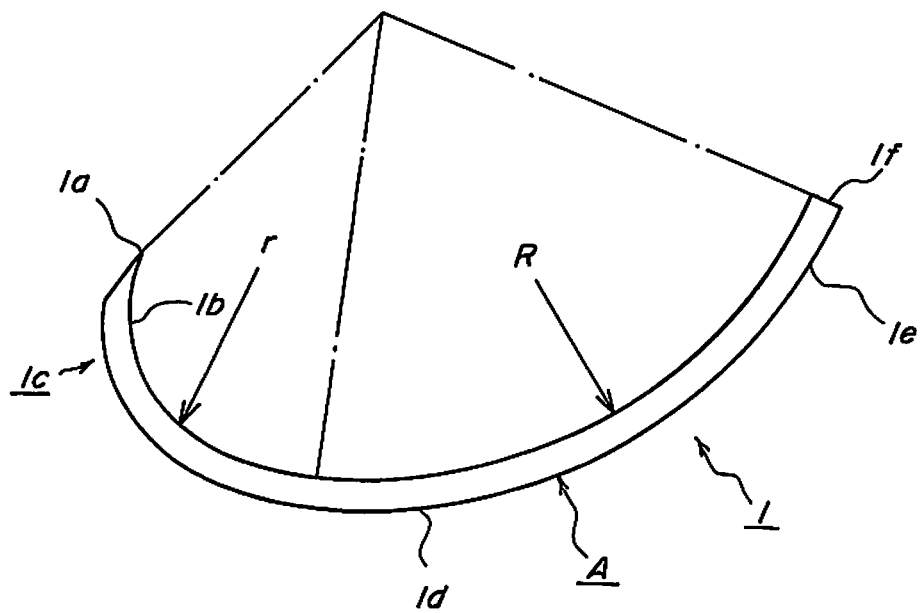
FIG. 1 is a view describing an example of a suturing needle (bi-curve suturing needle) curved at different curvature radii from the needle tip to the proximal end through the trunk portion.

A suturing needle
B, C bending apparatus
1 raw material
1a needle tip
1b cutting edge
1c cutting blade portion
1d trunk portion
1e proximal end
11 bending roller
12 belt
13a supply roll
13b winding roll
14 press roll
15 pressing member
20, 21 constricting member
20a, 20b, 21a, 21b supporting member

BEST MODE FOR CARRYING OUT THE INVENTION

The most preferred embodiments of a bending method and a bending apparatus for a suturing needle according to the present invention will be described below. The bending method for the suturing needle of the present invention includes performing a bending work by curving a raw material in the length direction from a needle tip having a distal end formed sharp or blunt to the proximal end through a tapered portion including the needle tip and a substantially linear trunk portion, and is realized by forming to a desired curved shape by changing the winding angle of the belt with respect to the bending roller.

In the present invention, the cross-sectional shape and the function of the suturing needle are not limited, and application can be made to any cross-sectional shape such as a round needle having a circular cross-section and without a cutting edge, and a cutting needle having a triangular cross-section and including a cutting edge in a range of a predetermined length from the needle tip.

The present invention is advantageous when applied to the bending work of configuring suturing needles respectively having a target curved shape by bending a plurality of raw materials set with different curved shapes in advance by one bending roller, and the bending work of when configuring suturing needles having a curved shaped with different curvature radius in the length direction with respect to one raw material, for example, so that the curvature radius at the needle tip portion is small and the curvature radius becomes greater from the tapered portion towards the trunk portion.

The material configuring the suturing needle is not particularly limited, and wire material and plate material made of steel represented by a piano wire, martensitic stainless steel, austenitic stainless steel, and the like may be used.

In particular, since the suturing needle is inserted to the living tissue to pass the suturing thread, the suturing needle needs to have a hardness that can easily pass the living tissue and rust preferably does not produce in the distributing step. In this viewpoint, a material that exhibits high hardness by work hardening and bending strength by the tissues stretched to a fiber-form by performing cold wire drawing process on the wire made of austenitic stainless steel at a predetermined surface reduction rate to stretch the tissues to a fiber-form is preferably used.

The bending roller is formed to a shaft rod-shape and has the outer circumferential surface formed to a forming surface, and is configured to rotate reciprocally. The diameter of the bending roller is not particularly limited, and may not necessarily match the curved shape of the target suturing needle. In other words, the diameter of the bending roller is preferably formed in view of conditions including the properties (e.g., spring back characteristics etc.) of the material configuring the raw material of the suturing needle.

The belt is wound to the outer circumferential surface of the bending roller to sandwich the raw material of the suturing needle with the outer circumferential surface, and forms the raw material by the relative pressure contact of the backup member and bending roller. Thus, the belt needs to have flexibility and strength so as not to easily break.

Therefore, any belt may be used without limiting the material and the like as long as the above condition is satisfied. Such belt includes a metal belt such as a steel belt, a stainless belt, and a brass belt, which belts can be selectively used. However, not limited to a metal belt, a synthetic resin belt that satisfies the above condition may be used.

The winding angle of the belt with respect to the bending roller is not particularly limited, and is preferably appropriately set in accordance with the curved shape of the target suturing needle. For instance, if the curved shape of the target suturing needle corresponds with the diameter of the bending roller, the winding angle of the belt with respect to the bending roller needs to be an angle such that the length the belt is wound to the bending roller is substantially equal to the length of the raw material.

If the curved shape of the target suturing needle is greater than the diameter of the bending roller, the winding angle of the belt with respect to the bending roller becomes smaller. The winding angle of the belt with respect to the bending roller in this case is preferably appropriately set according to conditions such as the diameter of the bending roller and the bending strength of the raw material.

FIRST EXAMPLE

Figure 2:
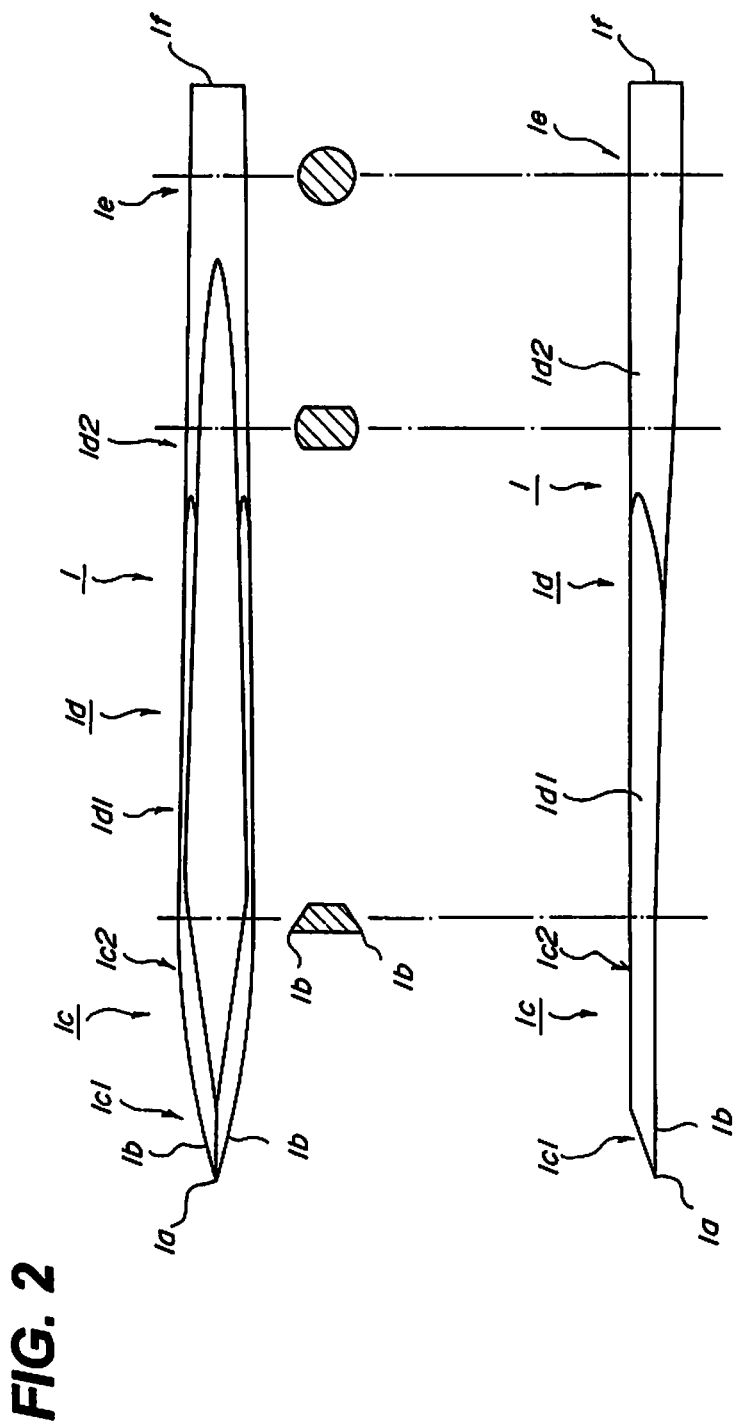
FIG. 2 is a view describing a configuration of the raw material immediately before bending the suturing needle illustrated in FIG. 1.
Figure 3:
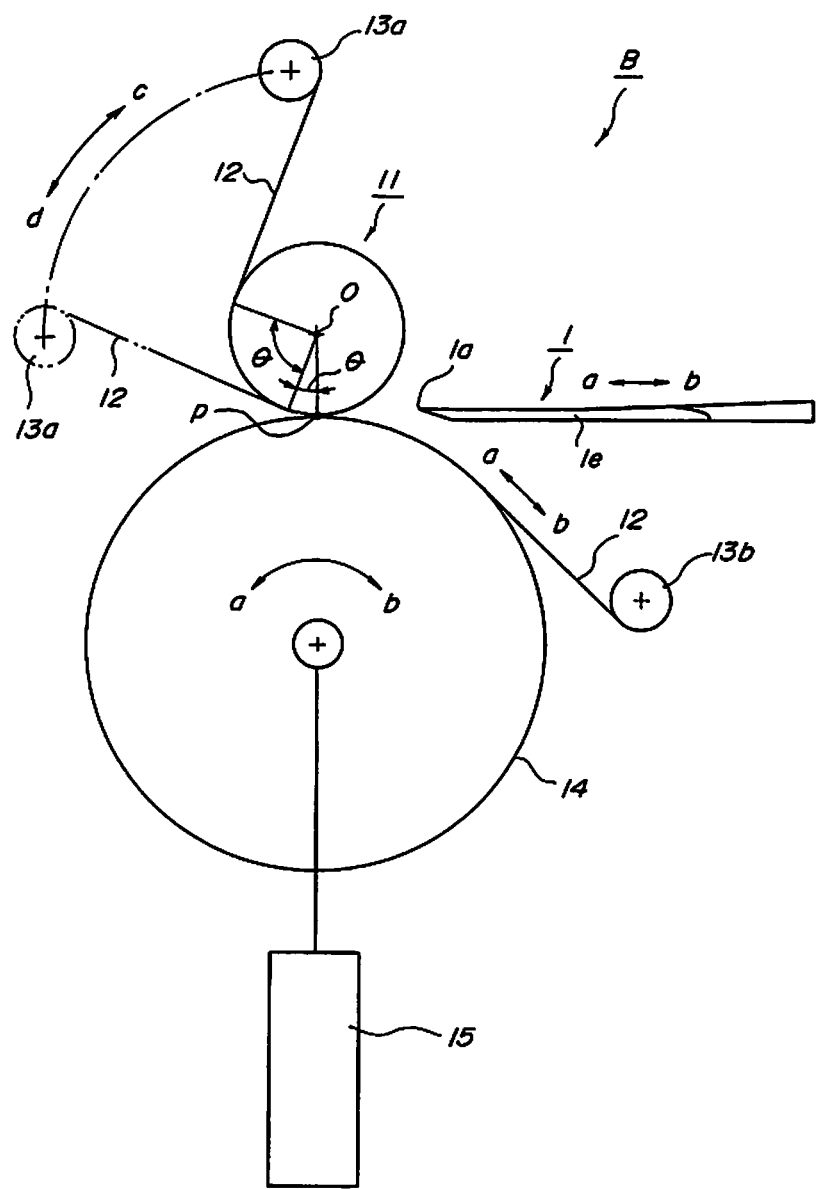
FIG. 3 is a view describing a configuration of a bending apparatus of the present example.

A first example of the bending apparatus for implementing the bending method according to the present invention will be described using the drawings. FIG. 1 is a view describing an example of a suturing needle (bi-curve suturing needle) curved at different curvature radii from the needle tip to the proximal end through the trunk portion. FIG. 2 is a view describing a configuration of the raw material immediately before bending the suturing needle illustrated in FIG. 1. FIG. 3 is a view describing a configuration of the bending apparatus of the present example. FIG. 4 is a view describing a state of bending to different curved shapes.

First, the suturing needle A having a curved shape with different curvature radii in the length direction will be described in FIGS. 1 and 2. This suturing needle A is an opthalmologic suturing needle called the bi-curve needle that is formed to a curved shape having different curvature radii from a needle tip $1a$ to an proximal end $1e$ through a cutting blade portion $1c$ formed with a cutting edge $1b$ and a trunk portion $1d$ from a raw material 1 having a thickness of about 0.1 mm to 0.4 mm.

In the present example, the portion from the needle tip $1a$ to the cutting blade portion $1c$ is curved at a radius r having small curvature radius, and the trunk portion $1d$ is curved at a radius R having large curvature radius. In particular, the curve at the radius r is formed in a very short range of up to the cutting blade portion $1c$ including the needle tip $1a$, and the radius r continuously increases to the radius R from the cutting blade portion $1c$ to the trunk portion $1d$ continuing to such range, so that the site corresponding to the trunk portion $1d$ curves at the radius R.

In the suturing needle A, the needle tip $1a$ is formed as a sharp pointed end so as to be inserted to the living tissue with small resistance. The cutting blade portion $1c$ continuing to the needle tip $1a$ is configured with a portion $1c1$ of triangular cross-section and a portion $1c2$ of trapezoidal cross-section continued, and the cutting edge $1b$ is formed at both sides of the bottom side across such portions $1c1$, $1c2$. The trunk portion $1d$ is configured with a portion $1d1$ of trapezoidal cross-section on the cutting blade portion $1c$ side and a portion $1d2$ of drum-shaped (a shape formed by two parallel straight lines and two arch lines swelled outside) cross-section continued, and is not formed with the cutting edge even at the bottom side of the portion $1d1$. Furthermore, the proximal end $1e$ is formed to a circular cross-section, and a stop-hole for attaching the suturing thread (not illustrated) is formed at an proximal end face $1f$.

In the present example, an austenite stainless steel wire formed to have a thickness of 0.4 mm by cold wire drawing process is used for the raw material 1 of the suturing needle A. This material has high hardness and bending strength, and the amount of spring back when the bending work is performed is great compared to the martensitic stainless steel of before being subjected to heat treatment.

A bending apparatus B will be described in FIG. 3. In the figure, a bending roller 11 is attached to a frame (not illustrated) so as to be rotatable reciprocally in the directions of the arrows a, b (winding direction and rewinding direction) and immovable other than being rotatable, and a flexible belt 12 is wound to the outer circumferential surface of the bending roller 11. The belt 12 is pulled out from a supply roll 13a arranged on the upstream side, sandwiched between the bending roller 11 and a press roll 14, and then wound to the winding roll 13b. The press roll 14 arranged on the lower side of the bending roll pressure contacts the bending roller 11 while sandwiching the belt 12 by means of a pressing member 15.

The thickness of the bending roller 11 is set in correspondence with the maximum radius at the curved site of the target suturing needle and thus is not uniquely set. However, the thickness is about 6 mm if the target suturing needle A is an opthalmologic suturing needle. The outer circumferential surface of the bending roller 11 having such thickness of about 6 mm contacts the raw material 1 to be formed as a forming surface to be bent.

An unused belt 12 is wound to the supply roll 13a and is pulled out by a predetermined length every time the bending work is performed on the raw material 1, where the belt 12 after the process is wound by the winding roll 13b. Thus, a new belt 12 is always supplied when performing the bending work on the new raw material 1 by winding the belt 12 by a predetermined length after performing the bending work on the raw material 1. Thus, the deformation of the belt 12 caused by performing the bending work does not become a failure when performing the bending work on the new raw material 1, and a more preferred forming can be implemented on the clean belt 12. The supply roll 13a is configured to be position movable in the directions of the arrows c, d along the outer circumferential surface with respect to the bending roller 11 while being wound with unused belt 12. The winding angle θ of the belt 12 with respect to the bending roller 11 becomes large when the supply roll 13a moves in the direction of the arrow c, and the winding angle θ becomes small when the supply roll 13a moves in the direction of the arrow d.

The supply roll 13a is configured to be position movable in the directions of the arrows c, d along the outer circumferential surface with respect to the bending roller 11 while being wounded with unused belt 12. The winding angle θ of the belt 12 with respect to the bending roller 11 becomes large when the supply roll 13a moves in the direction of the arrow c, and the winding angle θ becomes small when the supply roll 13a moves in the direction of the arrow d.

In the present example, the supply roll 13a is position movable in the directions of the arrows c, d on a circular arc having the center o of the bending roller 11 as the center, but the present invention is not necessarily limited to such configuration, and the supply roll 13a may linearly move in the horizontal direction or the diagonal direction. In either case, a construction, in which the winding angle θ of the belt 12 with respect to the bending roller 11 is changed by changing the position of the supply roll 13a, is substantially included in a construction changing the roller of the present invention along the outer circumferential surface of the bending roller.

The press roll 14 is constantly applied with substantially constant force by the pressing member 15 to pressure contact the bending roller 11. The pressing member 15 merely needs to have function of pressure contacting the press roll 14 to the bending roller 11 at substantially a constant force, and springs such as a push spring or a pull spring, air cylinders and hydraulic cylinders capable of holding the supply pressure of the fluid constant, and the like are preferably used.

In the present example, the pressing member 15 is configured by an air cylinder attached to a sub-frame for rotatably supporting the press roll 14.

In the bending apparatus B described above, the outer circumferential surface of the bending roller 11 and the press roll 14 pressure contact at point P as a reference point, and the bending work with respect to the raw material 1 is performed by rotating the bending roller 11 reciprocally in the directions of the arrows a, b.

The configuration of the drive device for rotating the bending roller 11 is not particularly limited, and may be driven through manual operation by the worker or may be driven by an electric motor configured to forward and reverse rotate at a constant angle. The bending roller 11 is preferably driven by a motor when there is a need to manufacture great amount of suturing needles A at one time.

The task of bending the raw material 1 illustrated in FIG. 2 with the bending apparatus B configured as above will now be described using FIG. 4. First, it is confirmed that the belt 12 at the position of point P is new and that the press roll 14 is pressure contacted with an appropriate force.

The curved shape set in advance to the target suturing needle is then confirmed, and the supply roll 13a is moved in the direction of the arrow a or the direction of the arrow b to set the winding angle θ of the belt 12 with respect to the bending roller 11 to realize such curved shape of the suturing needle.

For instance, if the curved shape of the target suturing needle has the same curvature radius from the needle tip to the trunk portion and such curvature radius is the same as the curvature radius of the outer circumferential surface of the bending roller 11, the supply roll 13a is moved in the direction of the arrow c so that the portion from the needle tip to the trunk portion of the raw material is constricted by the bending roller 11 and the belt 12.

Figure 4A:
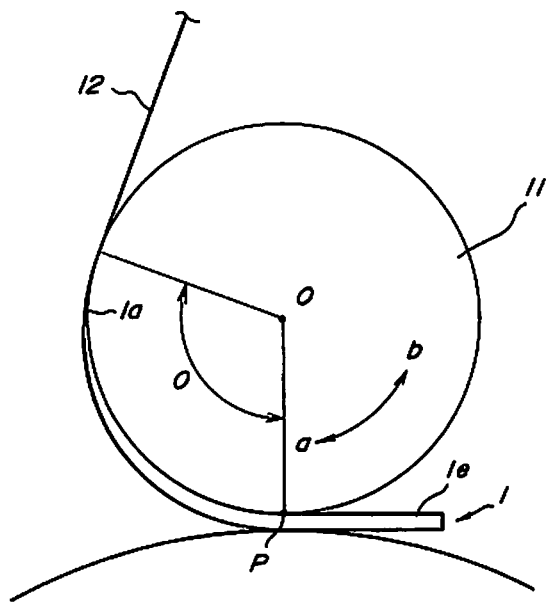
FIG. 4 is a view describing a state of bending to different curved shapes.

After setting the winding angle θ of the belt 12 with respect to the bending roller 11, the needle tip 1a of the raw material 1 is inserted between the bending roller 11 and the belt 12 at point P or the site where the bending roller 11 and the press roll 14 pressure contact, and the bending roller 11 is rotated in the direction of the arrow a, as illustrated in FIG. 4(a). With such rotation, the belt 12 and the press roll 14 respectively moves in the direction of the arrow a, and at the same time, the raw material 1 is taken in between the bending roller 11 and the belt 12 and transferred in the direction of the arrow a.

In this process, the raw material 1 is biased by the press roll 14 to pressure contact the outer circumferential surface of the bending roller 11, and is constricted to the bending roller 11 by the belt 12 and subjected to the bending work. The rotation angle of the bending roller 11 in the direction of the arrow a corresponds to the length from the needle tip 1a to the proximal end 1e of the raw material 1, and the raw material 1 is constricted while being sandwiched by the belt 12 and the bending roller 11 from the needle tip 1a to the proximal end 1e and subjected to the bending work.

As described above, after forming to the proximal end 1e with respect to the raw material 1 by rotating the bending roller 11 for a predetermined angle (angle from the needle tip 1a of the raw material 1 to the proximal end 1e through the trunk portion 1d) in the direction of the arrow a is finished, the bending roller 11 is rotated in the direction of the arrow b. With such rotation, the belt 12 and the press roll 14 move or rotate in the direction of the arrow b, so that the raw material 1 is discharged from between the bending roller 11 and the belt 12. The discharged raw material 1 has the portion from the needle tip 1a to the proximal end 1e bent to a curved shape having a curvature radius substantially the same as the curvature radius of the bending roller 11.

If the curved shape set in advance to the target suturing needle has a curvature radius greater than the curvature radius of the bending roller 11, the supply roll 13a is moved in the direction of the arrow d to change the winding angle θ of the belt 12 with respect to the bending roller 11. Here, to what angle to set the winding angle θ is appropriately set in view of various conditions such as the bending strength corresponding to the property of the raw material, the thickness, the diameter of the bending roller 11, and the like.

Figure 4B:
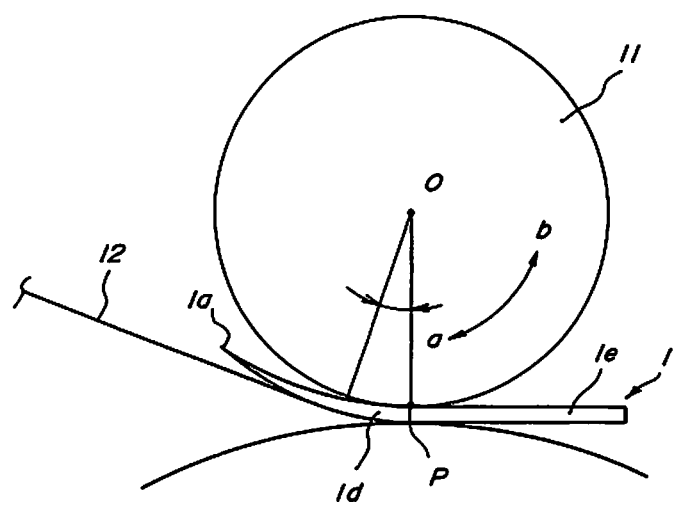

Then, as illustrated in FIG. 4(b), the needle tip 1a of the raw material 1 is inserted between the bending roller 11 and the belt 12 at point P or the site where the bending roller 11 and the press roll 14 pressure contact, and the bending roller 11 is rotated in the direction of the arrow a. With such rotation, the belt 12 and the press roll 14 are respectively moved in the direction of the arrow a, and at the same time, the raw material 1 is taken in between the bending roller 11 and the belt 12 and transferred in the direction of the arrow a.

In this process, at first, the raw material 1 has the needle tip 1a biased to the press roll 14 to pressure contact the outer circumferential surface of the bending roller 11, and constricted by the belt 12 and the bending roller 11 and subjected to the bending work. With the subsequent rotation of the bending roller 11 in the direction of the arrow a, the trunk portion 1d is constricted by the belt 12 and the bending roller 11 and subjected to the bending work, and at the same time, the needle tip 1a is released from the constriction by the belt 12 and the bending roller 11. Since the constricting region by the belt 12 and the bending roller 11 is short, the degree of bending work with respect to the needle tip 1a is small compared to the case of FIG. 4(a), so that the curved shape of the needle tip 1a has a curvature radius greater than the curvature radius of the bending roller 11.

When the needle tip 1a is discharged from the constricting region of the belt 12 and the bending roller 11 with the rotation of the bending roller 11 in the direction of the arrow a, the trunk portion 1d subsequently enters the constricting region. Since the constricting region by the belt 12 and the bending roller 11 with respect to the trunk portion 1d is also short, the degree of bending becomes small compared to the case of FIG. 4(a), so that the curved shape of the trunk portion 1d has a curvature radius greater than that of the bending roller 11.

With further rotation of the bending roller 11 in the direction of the arrow a, the trunk portion 1d and one part of the proximal end 1e are discharged from the constricting region by the belt 12 and the bending roller 11, and the raw material 1 has the portion from the needle tip 1a to the proximal end 1e bent to a curved shape having a curvature radius greater than the curvature radius of the bending roller 11.

The bending work with respect to the raw material 1 terminates when the rotation angle of the bending roller 11 in the direction of the arrow a corresponds to the length from the needle tip 1a to the proximal end 1e of the raw material 1. Thereafter, the bending roller 11 rotates in the direction of the arrow b, and the raw material 1, terminated with the bending work, is discharged. The discharged raw material 1 is bent to a curved shape in which the portion from the needle tip 1a to the proximal end 1e has a curvature radius greater than the curvature radius of the bending roller 11.

In particular, when the target suturing needle is the suturing needle A in which the portion from the needle tip 1a to the cutting blade portion 1c curved at a curvature radius r substantially the same as the diameter of the bending roller 11 and the portion from the trunk portion 1d to the proximal end 1e is curved at a curvature radius R greater than the curvature radius r, as illustrated in FIG. 1, the supply roll 13a is moved in advance in the direction of the arrow c and set at a position where the winding angle of the belt 12 with respect to the bending roller 11 is made large, the raw material 1 is inserted between the belt 12 and the bending roller 11 from point P in such state and the bending roller 11 is rotated in the direction of the arrow a.

The rotation of the bending roller 11 in the direction of the arrow a is continued, and the site from the needle point 1a to the cutting blade portion 1c is constricted by the belt 12 and the bending roller 11 and subjected to sufficient bending. Thereafter, the supply roll 13a is moved in the direction of the arrow d while continuing to rotate the bending roller 11 in the direction of the arrow a and continuing the bending work on the trunk portion 1d, so that the winding angle θ of the belt 12 with respect to the bending roller 11 becomes smaller. The bending force that acts on the trunk portion 1d of the raw material 1 becomes small with change in the winding angle θ, and the processing degree at the trunk portion 1d becomes small, and hence the curvature radius becomes greater than the needle tip 1a.

The portion from the needle tip 1a to the cutting blade portion is curved at the curvature radius r, the portion from the trunk portion 1d to the proximal end 1e is curved at the curvature radius R, and the range from the cutting blade portion 1c to the trunk portion 1d can be bent to the curved shape in which the curvature radius gradually and continuously changes from the curvature radius r to the curvature radius R by moving the position of the supply roll 13a set in the direction of the arrow c to the direction of the arrow d with the rotation of the bending roller 11 in the direction of the arrow a.

Furthermore, during the bending work with respect to the raw material 1, the needle tip 1a, the portion from the cutting blade portion 1c to the trunk portion 1d, and from the trunk portion 1d to the proximal end 1e can be bent to a curved shape having different curvature radius by changing the supply roll 13a from the position in the direction of the arrow c to the direction of the arrow d, and then further moving in the direction of the arrow c.

The winding θ of the belt 12 with respect to the bending roller 11 can be changed even by fixing the supply roll 12a and moving the press roll 14 along the outer circumference of the bending roller 11, which case is no different from moving the supply roll 13a along the outer circumference for the bending roller 11 when taking into consideration the point P or the contact site of the bending roller 11 and the press roll 14. In other words, the roller wound with the belt can be substantially moved along the outer circumferential surface of the bending roller even if the supply roll 13a is fixed and the press roll 14 is moved in such manner.

SECOND EXAMPLE

A bending apparatus according to a second example will now be described using the drawings. FIG. 5 is a view schematically describing the configuration of the main parts of the bending apparatus of the second example. In the figure, the same reference numerals are denoted for the sites having the same functions as the example described above, and the description thereof will be omitted.

A bending apparatus C illustrated in the figure is the same as the bending apparatus B other than that the belt 12 is suspended between a pair of constricting members 20, 21, and the bending roller 11 is configured to be position movable in the directions of the arrows e, f or the direction transversing the line (belt 12) connecting the constricting members 20, 21.

In the figure, the pair of constricting members 20, 21 are respectively made up of a plurality of supporting members 20a, 20b, 21a, 21b, and are respectively configured by a rotation shaft arranged on a frame or a rod-shaped member subjected to low abrasion process. The belt 12 is suspended between the constricting members 20, 21, and the bending roller 11 is arranged between the constricting members 20, 21 and is position movable in the directions of the arrows e, for the directions transversing the belt 12 that is suspended. The press roll 14 is also configured to be position movable in the directions of the arrows e, f same as the bending roller 11.

Figure 5A:
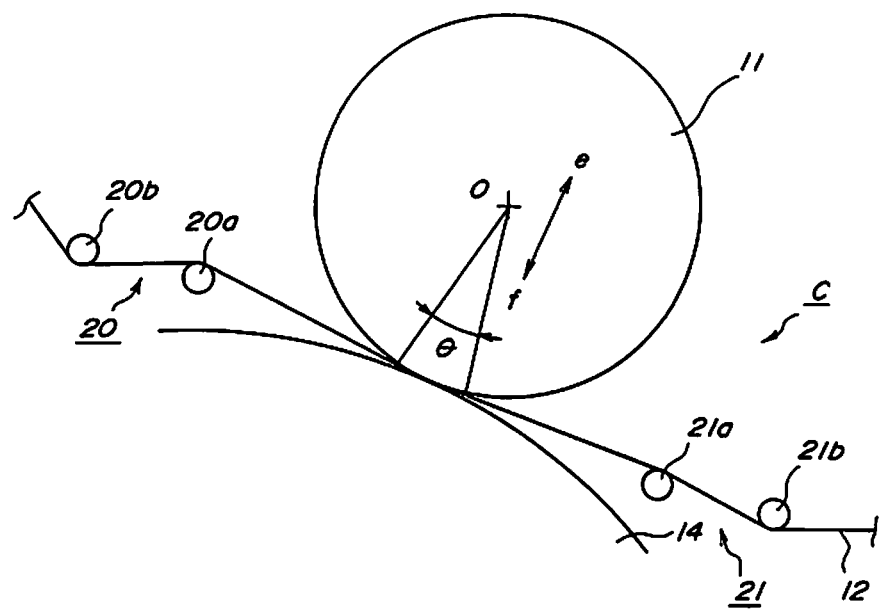
FIG. 5 is a view schematically describing a configuration of the main parts of a bending apparatus of a second example.
Figure 5B:
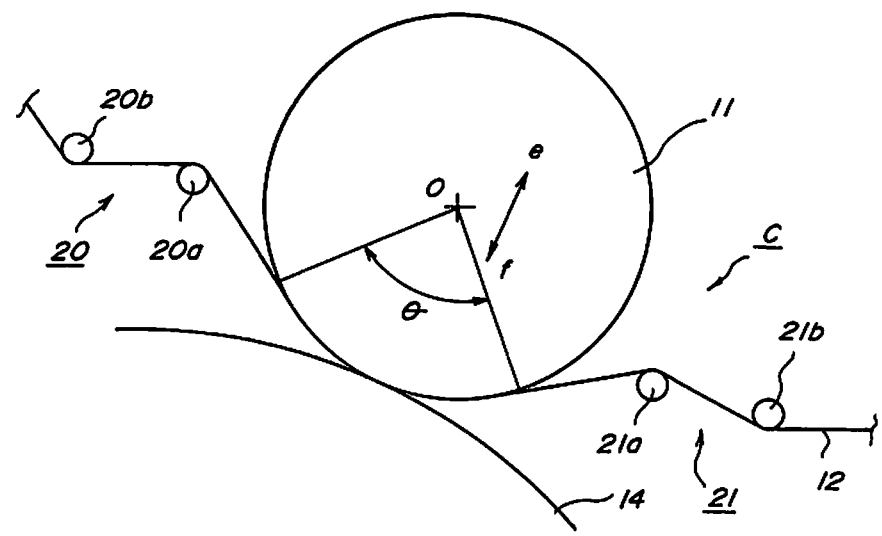

The winding angle θ of the belt 12 with respect to the bending roller 11 can be changed, as illustrated in FIGS. 5(a) and 5(b), by moving the bending roller 11 in the directions of the arrows e, f, and the bending work with respect to the raw material 1 can be performed, similar to the case of FIGS. 4(a) and 4(b), after setting the winding angle θ of the belt 12 with respect to the bending roller 11.

In the present example, the rotation shaft or the rod-shaped member is used for the constricting members 20, 21, but such members do not necessarily need to be used, and a roller may be arranged on each side of the bending roller 11 on the transfer path of the belt 12 illustrated in FIG. 3, and such roller may be used as the constricting member.

In the present example, the direction transversing the line connecting the pair of constricting members 20, 21 or the movement direction of the bending roller 11 merely needs to be a direction transversing the belt 12 suspended between the constricting members 20, 21, and may be a direction orthogonal to the belt 12 or a direction orthogonal thereto. The suturing needle A can be subjected to the bending work while pressure contacting the bending roller with only the belt 12 even if the press roll 14 is not present since the supporting members 20a, 21a are brought close to the bending roller at an interval of an extent of the diameter of the bending roller 11.

INDUSTRIAL APPLICABILITY

In the bending method according to the present invention, the bending work to a plurality of types of curved shapes can be performed with a specific bending roller, and is effectively used to form the bi-curve needle useful as an opthalmologic suturing needle or to form the distal end portion including the sharp needle tip to the same curved shape as the trunk portion and the proximal end.

The bending apparatus according to the present invention is advantageous as the bending method can be smoothly performed.

The invention claimed is:

1. A bending method for a medical suturing needle, the bending method comprising the steps of:
    sandwiching and contricting a raw material of the medical suturing needle between a bending roller and a belt, and
    reciprocally rotating the bending roller in a winding direction and a re-winding direction to curve the raw material, said step of reciprocally rotating includes changing a winding angle at which the belt is wound to the outer circumferential surface of the bending roller, and changing a constricting region with respect to the raw material of the medical suture needle so that the raw material is formed to have different curvature radii in each part of the raw material.

2. A bending apparatus for a medical suturing needle comprising:
    a reciprocally rotatable bending roller and
    a belt having such a flexibility as can be pressure contacted and wound on an outer circumferential surface of the bending roller, wherein a winding angle, at which the belt is wound to the outer circumferential surface of the bending roller, being capable of being changed so that a raw material has different curvature radii in each part of the raw material.

3. The bending apparatus for the medical suturing needle according to claim 2, wherein
    the belt having flexibility is formed to be longer than the raw material of the medical suturing needle and at least one side of a wound site wound on the bending roller is wound across a roller, and the position of the roller is changed along and relative to a position on the outer circumferential surface of the bending roller so as to be capable to change the winding angle at which the belt is wound on the outer circumferential surface of the bending roller.

4. The bending apparatus for the medical suturing needle according to claim 2, wherein
    the belt having flexibility is formed to be longer than the raw material of the medical suturing needle; and further comprising:
    a pair of constricting members for suspending the belt is arranged; wherein
    the bending roller is arranged between the pair of constricting members and is position movable in a direction transversing a line connecting the pair of constricting members; and
    the belt is suspended between the pair of constricting members and the position of the bending roller is changed in the direction transversing the line connecting the pair of constricting members to change the winding angle at which the belt is wound on the outer circumferential surface of the bending roller.

* * * * *